＊

US008483454B2

(12) United States Patent
Li (10) Patent No.: US 8,483,454 B2
(45) Date of Patent: Jul. 9, 2013

(54) METHODS FOR TISSUE CLASSIFICATION IN CERVICAL IMAGERY

(75) Inventor: Wenjing Li, Honolulu, HI (US)

(73) Assignee: STI Medical Systems, LLC, La Jolla, CA (US)

( * ) Notice: Subject to any disclaimer, the term of this patent is extended or adjusted under 35 U.S.C. 154(b) by 756 days.

(21) Appl. No.: 12/587,603

(22) Filed: Oct. 9, 2009

(65) Prior Publication Data

US 2010/0092064 A1    Apr. 15, 2010

Related U.S. Application Data

(60) Provisional application No. 61/196,159, filed on Oct. 10, 2008.

(51) Int. Cl.
*G06K 9/00* (2006.01)

(52) U.S. Cl.
USPC .......................................................... 382/128

(58) Field of Classification Search
USPC ........................................................... 382/128
See application file for complete search history.

(56) References Cited

U.S. PATENT DOCUMENTS

| | | | | |
|---|---|---|---|---|
| 5,257,182 A | * | 10/1993 | Luck et al. | 382/224 |
| 5,857,030 A | | 1/1999 | Gaborski et al. | |
| 5,982,917 A | | 11/1999 | Clarke et al. | |
| 6,026,323 A | | 2/2000 | Skladnev et al. | |
| 6,101,408 A | * | 8/2000 | Craine et al. | 600/425 |
| 6,135,965 A | | 10/2000 | Tumer et al. | |
| 6,198,838 B1 | | 3/2001 | Roehrig et al. | |
| 6,766,184 B2 | | 7/2004 | Utzinger et al. | |
| 7,257,243 B2 | | 8/2007 | Schmidt et al. | |
| 7,260,248 B2 | | 8/2007 | Kaufman et al. | |
| 7,309,867 B2 | | 12/2007 | Costa et al. | |
| 7,310,547 B2 | | 12/2007 | Zelenchuk | |
| 7,782,464 B2 | * | 8/2010 | Mujat et al. | 356/479 |
| 2006/0141633 A1 | | 6/2006 | Balas | |
| 2006/0184040 A1 | | 8/2006 | Keller et al. | |
| 2006/0257031 A1 | * | 11/2006 | Abramoff et al. | 382/224 |
| 2008/0058593 A1 | | 3/2008 | Gu et al. | |
| 2008/0132794 A1 | | 6/2008 | Alfano et al. | |
| 2008/0175465 A1 | * | 7/2008 | Jiang et al. | 382/131 |
| 2008/0226147 A1 | | 9/2008 | Hargrove et al. | |
| 2008/0240558 A1 | * | 10/2008 | Li et al. | 382/167 |
| 2009/0034824 A1 | * | 2/2009 | Li et al. | 382/133 |
| 2009/0046905 A1 | * | 2/2009 | Lange et al. | 382/128 |
| 2009/0198094 A1 | * | 8/2009 | Fenster et al. | 600/3 |
| 2009/0234237 A1 | * | 9/2009 | Ross et al. | 600/504 |
| 2010/0027863 A1 | | 2/2010 | Venkataraman et al. | |

OTHER PUBLICATIONS

Pogue, Brian W. et al., "Image analysis for discrimination of cervical neoplasia," Journal of Biomedical Optics, vol. 5, No. I, 72-82 (Jan. 2000).*

(Continued)

*Primary Examiner* — Luke Gilligan
*Assistant Examiner* — Robert Sorey
(74) *Attorney, Agent, or Firm* — Martin E. Hsia; Keri Ann K. S. Krzykowski (57) ABSTRACT

A rule-based unsupervised process for classifying cervical tissue by serially applying classifiers selected from the group that consists of determining size of texture region, opacity parameter, size of acetowhite regions, number of coarse and fine punctations, size of coarse and fine mosaics, size of atypical blood vessels and demographic data, so that the cervical tissue can be classified into no evidence of disease, low-grade dysplasia, high-grade dysplasia or cancer.

11 Claims, 8 Drawing Sheets

| Features | Variable Name |
|---|---|
| Size of texture region (% of Area) | SizeTx |
| Opacity Parameter (% of pixel value) | OpaIdx |
| Size of acetowhite regions (% of Area) | SizeAW |
| Size of acetowhite region near os region (% of Area) | SizeAWnearOs |
| Size of Coarse Mosaics (% of Area) | SizeCM |
| Size of Fine Mosaics (% of Area) | SizeFM |
| Number of Coarse Punctations (count) | NumCP |
| Number of Fine Punctations (count) | NumFP |
| Size of Atypical Vessels (mm) | SizeAV |
| Confidence Level | Confidence |

OTHER PUBLICATIONS

Ji, Qiang et al., "Texture analysis for classification of cervix lesions," IEEE Trans. Med. Imag. vol.19, No. 11, 1144-1149 (Nov. 2000).*
Ji, Qiang et al., "Classifying cervix tissue patterns with texture analysis," Pattern Recognition, vol. 33, 1561-1573 (2000).*
Srinivasan, Yeshwanth et al., "A probabilistic approach to segmentation and classification of neoplasia in uterine cervix images using color and geometric features," Proc. SPIE, vol. 5747, 995-1003 (2005).*
Li, Wenjing et al., "Detection and characterization of abnormal vascular patterns in automated cervical image analysis," LNCS—Advances in Visual Computing, vol. 4292, 1543-1552 (2006).*
Jia et al, "Automatic Image Quality Assessment for Uterine Cervical Imager", Medical Imaging 2006, Proc of SPIE vol. 6146,p. 61461B-1 to 61461B-12.*
De Bruin et al., "In Vivo Three-Dimensional Imaging of Neovascular Age-Related Macular Degeneration Using Optical Frequency Domain Imaging at 1050 nm." Investigative Ophthalmology & Visual Science, Oct. 2008, vol. 49, No. 10, p. 4545-4552.*
Balasubramanian, D.; Srinivasan, P.; Gurupatham, R.; , "Automatic Classification of Focal Lesions in Ultrasound Liver Images using Principal Component Analysis and Neural Networks," Engineering in Medicine and Biology Society, 2007. EMBS 2007. 29th Annual International Conference of the IEEE , vol., No., pp. 2134-2137, Aug. 22-26, 2007.*
Rahman, M.M.; Bhattacharya, P.; Desai, B.C.; , "A multiple expert-based melanoma recognition system for dermoscopic images of pigmented skin lesions," BioInformatics and BioEngineering, 2008. BIBE 2008. 8th IEEE International Conference on , vol., No., pp. 1-6, Oct. 8-10, 2008.*
Reid, R., Stanhope, C.R., Herschman, B.R., Crum, C.P., and Agronow, S.J., Genital warts and cervical cancer. IV. A colposcopic index for differentiating subclinical papillomaviral infection from cervical intraepithelial neoplasia, Am. J. Obstet. Gynecol. 149(8): 815-823. 1984.
Reid, R. and Scalzi, P., Genital warts and cervical cancer. VII. An improved colposcopic index for differentiating benign papillomaviral infection from high-grade cervical intraepithelial neoplasia. Am. J. Obstet. Gynecol. 10, pp. 153:611-618, 1985.
Kierkegaard, O., Byralsen, C., Hansen, K.C., Frandsen, K.H., and Frydenberg, M., Association between colposcopic findings and histology in cervical lesions: the significance of the size of the lesion, Gynecol. Oncol. 57(1), pp. 66-71. 1995.
Dickman, E.D., Doll, T.I., Chiu, E., and Ferris, D.G., Identification of cervical neoplasia using a simulation of human vision, J. Low. Genit. Tract Dis. 5(3), pp. 144-152, 2001.
Ferris, D.G., Lawhead, R.A., Dickman, E.D., Holtzapple, N., Miller, J.A., Grogan, S. et al., Multimodal hyperspectral imaging for the noninvasive diagnosis of cervical neoplasia, J. Low. Genit. Tract Dis. 5(2), pp. 65-72, 2001.
Lafferty, J., McCallum, A., and Pereira, F., Conditional random fields: Probabilistic models for segmenting and labeling sequence data. Proc. 18th International Conference on Machine Learning, pp. 282-289, 2001.
Rubin, M.M. and Barbo, D.M., Ch. 9a: Colposcopic assessment system. in colposcopy: principles and practice, Editors Apgar, B.S., Brotzman, G.L., and Spitzer, M., pp. 187-195, W.B. Saunders Company, Philadelphia, 2002.
Huh, W.K., Cestero, R.M., Garcia, F.A., Gold, M.A., Guido, R.S., McIntyre-Seltman, K. et al., Optical detection of high-grade cervical intraepithelial neoplasia in vivo: results of a 604-patient study, Am. J. Obstet. Gynecol. 190(5), pp. 1249-1257, 2004.
Ferris, D.G. and Litaker, M., Interobserver agreement for colposcopy quality control using digitized colposcopic images during the ALTS trial, J. Low. Genit. Tract Dis. 9(1), pp. 29-35, 2005.
Lange, H. and Ferris, D.G., Computer aided-diagnosis (CAD) for colposcopy; Proc. SPIE 5747, pp. 71-84, 2005.
Jeronimo, I., Massad, L.S., Castle, P.E., Wacholder, S., and Schiffman, M., Interobserver agreement in the evaluation of digitized cervical images, Obstet. Gynecol. 110(4), pp. 833-840, 2007.
Kendrick, J.E., Huh, W.X., and Alvarez, R.D., LUMA cervical imaging system, Expert Review of Medical Devices 4 (2), pp. 121-129, 2007.
Park, S.Y., Follen, M., Milbourne, A., Rhodes, H., Malpica, A., Mackinnon, N. et al., Automated image analysis of digital colposcopy for the detection of cervical neoplasia, J. Biomed. Opt. 13(1), pp. 014029-1-014029-10, 2008.
Li, W., van Raad, V., Gu, J., Hansson, U., Hakansson, J., Lange, H., and Ferris, D., Computer-aided diagnosis (CAD) for cervical cancer screening and diagnosis: a new system design in medical image processing, Lecture Notes in Computer Science, LNCS, pp. 240-250, 2005.

* cited by examiner

FIG 1

| Features | Variable Name |
|---|---|
| Size of texture region (% of Area) | SizeTx |
| Opacity Parameter (% of pixel value) | OpaIdx |
| Size of acetowhite regions (% of Area) | SizeAW |
| Size of acetowhite region near os region (% of Area) | SizeAWnearOs |
| Size of Coarse Mosaics (% of Area) | SizeCM |
| Size of Fine Mosaics (% of Area) | SizeFM |
| Number of Coarse Punctations (count) | NumCP |
| Number of Fine Punctations (count) | NumFP |
| Size of Atypical Vessels (mm) | SizeAV |
| Confidence Level | Confidence |

METHODS FOR TISSUE CLASSIFICATION IN CERVICAL IMAGERY

This application claims the benefit of U.S. Provisional Patent Application No. 61/196,159 filed Oct. 10, 2008.

TECHNICAL FIELD

The present invention generally relates to medical imaging, and more specifically to the computer aided detection and diagnosis of uterine cervical cancer and pre-cancerous lesions using methods for cervical tissue identification and classification.

BACKGROUND ART

This invention is being disclosed in connection with cervical cancer. Uterine cervical cancer is the second most common cancer in women worldwide, with nearly 500,000 new cases and over 270,000 deaths annually (http://www-depdb.iarc.fr/globocan2002.htm, incorporated herein by reference) Colposcopy is a diagnostic method used to detect cancer precursors and cancer of the uterine cervix (B. S. Apgar, Brotzman, G. L. and Spitzer, M., Colposcopy: Principles and Practice, W.B. Saunders Company: Philadelphia, 2002, incorporated herein by reference). CAD ("computer aided diagnosis") for colposcopy represents a new application of medical image processing. The inventors have developed a CAD system that mimics or emulates the diagnostic process used by colposcopists to assess the severity of abnormalities (Lange H. and Ferris, Daron G.; Computer-Aided-Diagnosis (CAD) for colposcopy; SPIE Medical Imaging 2005; SPIE Proc. 5747, 2005, incorporated herein by reference).

Colposcopists form colposcopic impressions based on different macroscopic epithelial (relating to membranes) features within cervical tissue. Colposcopic grading systems provide a structured, systematic method to critically analyze cervical findings. A systematic approach, once learned and mastered, becomes routine and is extraordinarily beneficial. Colposcopic grading systems also allow colposcopists to form more accurate colposcopic impressions. Well-designed colposcopic scoring systems enhance colposcopic reproducibility. Colposcopic grading systems are also helpful when attempting to select the most appropriate biopsy site, particularly when large, complex lesions (abnormal growths) of the cervix are encountered.

Scoring schemes, like the Reid's colposcopic index, are an aid for making colposcopic diagnoses (Reid R, Scalzi P. Genital warts and cervical cancer. VII. An improved colposcopic index for differentiating benign papillomaviral infection from high-grade cervical intraepithelial neoplasia. Am J Obstet Gynecol 1985; 153:611-618, incorporated herein by reference; Reid, R., Stanhope, C. R., Herschman, B. R., Crum, C. P., and Agronow, S. J., Genital warts and cervical cancer. IV. A colposcopic index for differentiating subclinical papillomaviral infection from cervical intraepithelial neoplasia, Am. J. Obstet. Gynecol. 149(8): 815-823. 1984, incorporated herein by reference) based on various features, including margin or border of lesion (abnormal growth), color of lesion following application of 5% acetic acid solution, blood vessel characteristics within the lesion, and response of the lesion to the application of Lugol's iodine solution. These features are individually assessed and scored before the scores of all features are combined to yield a composite score that grades disease severity. The Reid index differentiates low-grade cervical disease from high-grade disease. Consequently, the Reid Colposcopic Index (RCI) is not designed to discriminate premalignant from malignant cervical neoplasia. Nonetheless, the index provides a popular means of standardizing the evaluation of cervical neoplasia.

Rubin and Barbo (Rubin, M. M. and Barbo, D. M., Ch. 9a: Rubin and Barbo Colposcopic Assessment System, in Colposcopy: Principles and practice, eds. Apgar, B. S., Brotzman, G. L., and Spitzer, M., pp. 187-195. W.B. Saunders Company, Philadelphia, 2002, incorporated herein by reference) developed an assessment method that retains the best descriptors of some of the previous colposcopic grading systems, but eliminates the numbers, which can be confusing. In addition, it expands the system to include descriptors for normal findings. More importantly, it includes descriptors that focus the clinician's pattern recognition process on the possibility of microinvasive or frankly invasive disease. For example, it not only measures the intensity of the Acetowhite epithelial changes but also addresses other color-tone changes, such as red, yellow, and dull gray, that correlate more with the presence of invasive cancer.

Other factors that warrant consideration include a patient's age and the size and distribution of lesions. Cancer of the cervix is rare in patients younger than 25 years old. The majority of high-grade squamous intraepithelial disease (specifically CIN3) is found in women between 28 and 32 years of age. CIN1 lesions tend to be relatively small. The mean length of CIN1 lesions is approximately 2.8 mm (millimeters or thousandths of a meter). However, these lesions can reach a maximum length of 11.5 mm. In comparison, CIN2 and CIN3 lesions are larger. The mean (average) length of CIN2 and CIN3 are 5.8 mm and 7.6 mm respectively. Their maximum lengths are 18.2 mm and 20.6 mm respectively. Low-grade lesions may occupy only one quadrant of the cervix or a small percentage of the surface area of the ectocervix. The distribution of CIN1 varies from unifocal (lesion occurring at a single location) to multifocal (lesions occurring at multiple locations). Multiple, distinct, small, randomly scattered lesions are characteristic of CIN1.

CIN2 is invariably seen within the transformation zone (TZ). The TZ is the region of the cervix where the columnar epithelium has been replaced by the new metaplastic squamous epithelium. In contrast to CIN1, which may be found outside the TZ. CIN 2 may be multifocal, but a unifocal lesion is more common. Satellite lesions are not usually representative of CIN 2. Colposcopists will usually find CIN2 along the squamous-columnar junction (SCJ), located either on the ectocervix or within the endocervical canal.

CIN 3 lesions tend to be confluent (flowing together or blended into one), and longer and wider than CIN 1 or CIN 2 lesions. CIN 3 is usually located within the central portion of the cervix, inside the inner curve towards the external os. CIN 3 is rarely occult (hidden from the eye) when present on the ectocervix. The linear length of CIN 3 lesions, defined as the distance over the tissue surface between caudal (at or near the posterior end of the body) and cephlad (toward the head or anterior of the body) edges, varies between 2 mm to 22 mm. Mean linear lengths range from 6 mm to 10 mm. Long linear lesions—those greater than 10 mm, particularly when there is endocervical involvement—are always suspicious for cancer. As the surface area of lesions increases to more than 40 sq mm, so should the suspicion for cancer. It has been reported that the size of transformation zone (TZ), the size of lesions (abnormal growths), distinct margins, the vascular pattern (the pattern of blood vessels), and acetowhite color (color after the application of acetic acid) were significantly associated with the histological grade and demonstrated that the size of cervical lesion might be of clinical importance (Kierkegaard, O., Byralsen, C., Hansen, K. C., Frandsen, K. H., and Frydenberg, M., Association between colposcopic findings and histology in cervical lesions: the significance of the size of the lesion, Gynecol. Oncol. 57(1): 66-71. 1995, incorporated herein by reference).

Evidence based medicine (EBM) is defined as "the conscientious, explicit and judicious use of current best evidence in making decisions about the care of individual patients". In EBM, human perception and interpretation are considered highly valuable in diagnostic interpretation. However, human assessment can be subjective and have low inter-observer agreement (Ferris, D. G. and Litaker, M., Interobserver agreement for colposcopy quality control using digitized colposcopic images during the ALTS trial, J. Low. Genit. Tract Dis. 9(1): 29-35, 2005, incorporated herein by reference; Jeronimo, J., Massad, L. S., Castle, P. E., Wacholder, S., and Schiffman, M., Interobserver Agreement in the Evaluation of Digitized Cervical Images, Obstet. Gynecol. 110(4): 833-840, 2007, incorporated herein by reference).

Computers can be programmed to perform reasoning tasks and can be used for solving diagnostic problems. Colposcopic grading systems have been used by colposcopists for more than 40 years to derive clinical diagnoses. Colposcopists derive the colposcopic features of a patient qualitatively through a visual exam using a colposcope, determine the extent of disease and initiate patient management based on their experience. The procedure takes about ten or fifteen minutes in a gynecologist's office. Due of the subjective nature of the exam, the accuracy of colposcopy is highly dependent upon the colposcopist's experience and expertise. A computer implemented colposcopic scoring algorithm that utilizes quantified colposcopic features is desirable to provide physicians a suggested diagnostic decision.

Most existing tissue classification systems rely on statistical approaches. One example is the Georgia Tech Vision (GTV) system (Dickman, E. D., Doll, T. J., Chiu, C. K., and Ferris, D. G., Identification of Cervical Neoplasia Using a Simulation of Human Vision, Journal of Lower Genital Tract Disease 5(3): 144-152, 2001, incorporated herein by reference), a generic computer vision system inspired by the human vision system, to recognize normal and abnormal cervical features. Another example is the Multimodel Hyperspectral Imaging (MHI) system for the noninvasive diagnosis of cervical neoplasia (Ferris, D. G., Lawhead, R. A., Dickman, E. D., Holtzapple, N., Miller, J. A., Grogan, S. et al., Multimodal hyperspectral imaging for the noninvasive diagnosis of cervical neoplasia, J. Low. Genit. Tract Dis. 5(2): 65-72, 2001, incorporated herein by reference). Recently, a reflectance fluorescence system used to differentiate high grade intraepithelial lesions from normal or low grade intraepithelial lesions has been reported (Park, S. Y., Follen, M., Milbourne, A., Rhodes, H., Malpica, A., Mackinnon, N. et al., Automated image analysis of digital colposcopy for the detection of cervical neoplasia, J. Biomed. Opt. 13(1): 014029-1-014029-10, 2008, incorporated herein by reference). Further, a successful optical system LUMA™ for in-vivo (in the living body) detection of high-grade cervical intraepithelial neoplasia has also been reported (Huh, W. K., Cestero, R. M., Garcia, F. A., Gold, M. A., Guido, R. S., McIntyre-Seltman, K. et al., Optical detection of high-grade cervical intraepithelial neoplasia in vivo: results of a 604-patient study, Am. J. Obstet. Gynecol. 190(5): 1249-1257. 2004, incorporated herein by reference; Kendrick, J. E., Huh, W. K., and Alvarez, R. D., LUMA Cervical Imaging System, Expert Review of Medical Devices 4(2): 121-129, 2007, incorporated herein by reference). In the LUMA™ system, diagnostic scans of the entire human cervix are performed following acetic acid application employing three integrated optical measurements: laser-induced fluorescence spectroscopy, white light diffuse reflectance spectroscopy, and video imaging. Further, multivariate classification algorithms were included to exploit spectral differences in the interaction of specific light sources with different cervical tissue types.

Another in vivo detection and quantitative grading system called DySIS™ (Dynamic Spectral Imaging System) has been reported recently (Forthphotonics, DySIS:Dynamic Spectral Imaging System, http://www.forth-photonics.gr/dysis.php?page=dysis-trials2008, incorporated herein by reference; Soutter, W. P., Diakomanolis, E., Lyons, D., and Haidopoulos, D., Dynamic Spectral Imaging—In Vivo Detection and Quantitative Grading of Cervical Neoplasia, ASCCP 2008 Meeting Abstract. Journal of Lower Genital Tract Disease 12(2): 160, 2008, incorporated herein by reference). DySIS™ is the first CE-marked (CE mark is a mandatory conformity mark on many products placed on the single market in the European Economic Area (EEA)—The CE marking certifies that a product has met EU health, safety, and environmental requirements, which ensure consumer safety) device to utilize both digital and dynamic spectral imaging technology for assisting automated (and user independent) detection and mapping of cervical neoplasia (lesions or tumors) in vivo.

Figure 1:
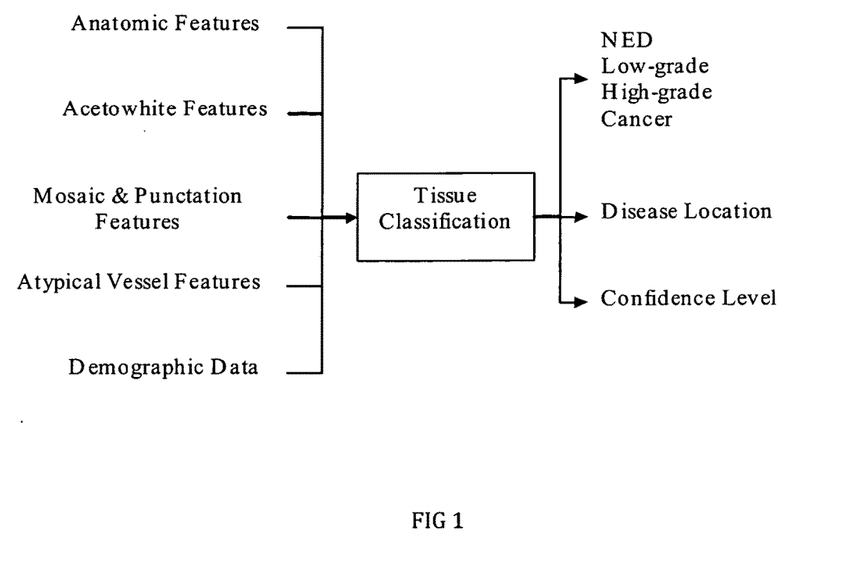
FIG. 1 is a flowchart showing an overview of the present invention.

The present invention is a computer aided detection technology based on a colposcopic grading system to accurately assess and identify low-grade lesions, high-grade lesions and cancer. It is different from statistical learning approaches listed in the prior art. The present invention is a rule based approach following colposcopy which accumulates the evidence of disease using morphological evaluation of epithelium and blood vessels. In statistical learning, a diagnostic decision is based on the statistical features derived from a huge amount of training data via cross validation. Therefore, it is a supervised learning approach based on training data and statistics theory. The current invention transfers the qualitative grading rules in modern colposcopy into a quantified computer program. It does not require any training from the data. It is an un-supervised approach based on prior medical knowledge. A flowchart showing an overview of the present invention is shown in FIG. 1. Prior to applying the tissue classification algorithm of the present invention, other methods are first applied to extract information which is used as the input to the tissue classification algorithm. The other methods include anatomic features algorithms, acetowhite feature extraction algorithms, mosaic and punctation detection algorithms (for example, W. Li and A. Poirson, Detection and characterization of abnormal vascular patterns in automated cervical image analysis, *Lecture Notes in Computer Science—Advances in Visual Computing* 4292, Second International Symposium, ISVC 2006, Lake Tahoe, Nev., November 2006 Proceedings, Part II, 627-636 (Springer 2006), incorporated herein by reference), and atypical vessels extraction algorithms (as disclosed in co-pending, commonly assigned patent application entitled "Methods for Detection and Characterization of Atypical Vessels in Cervical Imagery" filed Aug. 1, 2008, Ser. No. 12/221,328 incorporated herein by reference). The outputs of these methods serve as inputs for the present tissue classification method described herein. The tissue classification method is applied to image data of a cervix taken before and after applying acetic acid in real time during a clinical exam, as well as demographic data of the subject, such as age. The output of the tissue classification method includes a diagnostic decision with the following findings: the type of lesion (Normal/NED ("No Evidence of Disease"), Low-grade dysplasia, High-grade dysplasia, or cancer); disease location or the location of the high-grade (CIN 2 and CIN 3) lesions; and the confidence level of the decision.

The following patents and patent applications may be considered relevant to the field of the invention:

U.S. Pat. No. 7,309,867 to Costa et al., incorporated herein by reference, discloses methods for determining the probability that a given region of tissue sample contains tissue of given category, such as CIN, CIN II/III normal squamous, normal columnar, and metaplasia by utilizing a combination of statistical and non statistical classification techniques and by combining spectral data and image data.

U.S. Pat. No. 7,310,547 to Zelenchuk, incorporated herein by reference, discloses a system and method for the in situ discrimination of health and diseased tissue. It includes a fiberoptic probe to direct ultraviolet illumination onto a tissue specimen and to collect the fluorescent response radiation. The response radiation is observed at three selected wavelengths, one of which corresponds to an isosbestic point. In one example, the isosbestic point occurs at about 431 nm. The intensities of the observed signals are normalized using the 431 nm intensity. A score is determined using the ratios in a discriminant analysis. The tissue under examination is resected or not, based on the diagnosis of disease or health, according to the outcome of the discriminant analysis.

U.S. Pat. No. 7,260,248 to Kaufman et al., incorporated herein by reference, discloses methods of relating a plurality of images based on measures of similarity. The methods are useful in segmenting a sequence of colposcopic images of tissue. The methods can be applied to determine tissue characteristics in acetowhitening testing of cervical tissue. It discloses a method of determining a tissue characteristic that includes obtaining a plurality of images of a tissue; determining a relationship between two or more regions in the images; segmenting the images based on the relationship; and determining a characteristic of the tissue based on the segmentation. The determining step includes characterizing the tissue as either normal, CIN I, CIN II, CIN III or CIN II/III.

U.S. Pat. No. 6,766,184 to Utzinger et al., incorporated herein by reference, discloses methods and an apparatus for generating multispectral images of tissue. The image may be used for cervical cancer detection. A primary radiation is produce with a illumination source and filtered to select a first wavelength and first polarization. Tissue is illuminated with the filtered primary radiation to generate a secondary radiation, which is filtered to select a second wavelength and second polarization. The filtered secondary radiation is collected with a detector, and a plurality of multispectral images of the tissue is generated according to different combination of the first and second wavelengths and polarizations.

U.S. Pat. No. 6,198,838 to Roehrig et al., incorporated herein by reference, discloses a method and system for detecting suspicious portions of digital mammograms by using independently calculated mass and spiculation information. The method is used in a computer aided diagnosis system that is designed to bring suspicious or possibly cancerous lesions in fibrous breast tissue to the attention of a radiologist or other medical professional. In a preferred embodiment, spiculation information and mass information are independently calculated, with the computed spiculation information not being dependent on results of the mass information computation, thus leading to greater reliability.

U.S. Pat. No. 6,135,965 to Tumer et al., incorporated herein by reference, discloses an apparatus and method for spectroscopic detection of tissue abnormality in cervical tissue using neural networks to analyze in vivo measurements of fluorescence spectra.

U.S. Pat. No. 5,857,030 to Gaborski et al., incorporated herein by reference, discloses an automated method and system for digital image processing of radiologic images including a pre-processing stage of filtering, preliminary selection phase of segmentation, and a pattern classification phase that includes neural network classification.

U.S. Pat. No. 5,982,917 to Clarke et al., incorporated herein by reference, discloses a computer-assisted diagnostic (CAD) method and apparatus for the enhancement and detection of suspicious regions in digital x-ray images.

U.S. Patent Publication No. 2006/0141633 to Balas, incorporated herein by reference, discloses a method and apparatus for in vivo detection and mapping of alterations caused by biochemical and/or functional characteristics of epithelial tissues during the development of cancer.

U.S. Patent Publication No. 2006/0184040 to Keller et al., incorporated herein by reference, discloses a method and device for detecting a tissue abnormality whereby the method comprises emitting light from a light source onto the tissue; directing light emitted reflected from the tissue via the optics to the multiple wavelength imaging optical subsystem, and isolating one or more wavelengths or wavelength bands of interest; directing the one or more wavelengths or wavelength bands of interest to the one or more imaging devices, and using the devices to record images of the one or more wavelengths or wavelength bands of interest; transferring image data from the images to a computational system; and analyzing the images for one or more spectral patterns associated with tissue abnormalities.

U.S. Patent Publication No. 2008/0058593 to Gu et al., incorporated herein by reference, discloses a process for providing computer aided diagnosis from video data of an organ during an examination with an endoscope, comprising analyzing and enhancing image frames from the video and detecting and diagnosing any lesions in the image frams in real time during the examination. Further, the image data may be used to create a three-dimensional reconstruction of the organ.

DISCLOSURE OF THE INVENTION

The present invention described herein and more fully below, comprises a rule-based unsupervised process for classifying cervical tissue into a class, comprising applying a classifier that includes a set of classifier rules to cervical tissue, obtaining a final prediction by applying selected classifier rules serially, wherein, the applying step is performed using classifier rules selected from the group consisting of determining size of texture region, opacity parameter, size of acetowhite regions, number of coarse and fine punctations, size of coarse and fine mosaics, size of atypical blood vessels and demographic data, whereby the cervical tissue can be classified into no evidence of disease, low-grade dysplasia, high-grade dysplasia or cancer.

If the texture region is greater than approximately 1% of the area of the cervix, and if the opacity parameter is less than approximately 4% of the pixel value or greater than approximately 12% of the pixel value, a final prediction of no evidence of disease is obtained.

If the texture region is greater than approximately 1% of the area of the cervix, said opacity parameter is between approximately 4% of the pixel value and approximately 12% of the pixel value, the size of the acetowhite region is greater than 7% of the area of the cervix, and if the size of the acetowhite region near the os is greater than 0% of the area of the cervix, then a final prediction of high grade dysplasia is obtained.

If the texture region is greater than approximately 1% of the area of the cervix, if said opacity parameter is between approximately 4% of the pixel value and approximately 12% of the pixel value, the size of the acetowhite region is less than 7% of the area of the cervix, and there is no acetowhite region near the os, then a final prediction of low grade dysplasia is obtained.

If the texture region is less than approximately 1% of the area of the cervix, and if the opacity parameter is less than 5% of the pixel value, the number of coarse punctations is less than 2, and there are no coarse mosaic vessels, then a final prediction of low grade dysplasia is obtained.

If the texture region is less than approximately 1% of the area of the cervix, and the opacity parameter is greater than 8% and the size of the acetowhite region near the os is greater than 0.5% and the number of coarse punctations is greater than 100, and there are no coarse mosaic vessels, and the size of atypical vessels is greater than 0.5 millimeters, then a prediction of cancer is obtained.

If the texture region is less than approximately 1% of the cervix, and the opacity parameter is greater than 8% and the size of the acetowhite region near the os is greater than 0.5% and the number of coarse punctations is greater than 100, and there are no coarse mosaic vessels, and the size of abnormal vessels is greater than 0.5 millimeters, then a prediction of cancer is obtained.

If the texture region is less than approximately 1% of the area of the cervix, and if the opacity parameter is greater than 5% of the pixel value, the size of the acetowhite region near the os is less than 0.5% of the pixel value, the number of coarse punctation vessels is less than 100, coarse mosaic vessels are not present, and the size of atypical blood vessels is less than 0.5%, then a decision of high grade dysplasia is obtained.

BEST MODE FOR CARRYING OUT THE INVENTION (1) Pre-Method Applications

The presently preferred embodiment of the invention described herein preferably uses the output of several pre-method applications (the output being certain parameters described in FIG. 2) as the input for the tissue classification method. Many of the parameters or variables are described as a percentage of that particular feature's area versus the total area of the cervix in the image. The punctation feature is defined as the number of punctations present in the image. The size of atypical blood vessels is preferably calculated in millimeters (mm).

The process begins by collecting digital color images (using red, green, and blue channels or RGB) of the cervix—one before and one after the application of acetic acid. Preferably, the image is cross-polarized to suppress specular reflection (glint) and calibrated. Next, several pre-method applications including anatomic feature extraction, acetowhite feature extraction, mosaic and punctation detection, and atypical vessel extraction are applied.

The anatomic feature extraction preferably includes detection of the cervix, removal of the vaginal wall (both vertical and horizontal), os detection, columnar epithelium detection, and texture region (abnormal/metaplasia) detection.

Acetowhite feature extraction preferably includes applying acetic acid to an anatomic region of interest to produce acetowhite regions; taking at least one post acetic acid image of the acetowhite regions; detecting an anatomic region of interest having epithelial cells; extracting texture information from the post acetic acid image to define a texture region; extracting color information from the post acetic acid image to define a color region; and combining the texture region and the color region to create a candidate acetowhite region. Preferably, it also comprises: obtaining at least one pre acetic acid image of the epithelial cells; registering the acetowhite regions in one of the pre acetic acid images and in one of the post acetic acid images to form registered images of the acetowhite regions; and extracting an opacity parameter from the registered images of the acetowhite regions, as disclosed in co-pending, commonly assigned patent application entitled "Computerized Image Analysis for Acetic Acid Induced Cervical Intraepithelial Neoplasia" filed Aug. 4, 2008, Ser. No. 12/221,645, incorporated herein by reference. That application disclosed an opacity parameter created by clustering the differences in temporal changes between the registered pre and post acetic acid images. The opacity parameter provides high predictive value for lesion diagnosis—normal and low grade lesions have much lower opacity than high grade lesions and cancer cases. Other opacity parameter extraction methods can also be used, including ratio imaging in different color spaces.

In one preferred embodiment of the invention, the color difference of the a channel in CIE-Lab color space is used for opacity parameter extraction. In another preferred embodiment of the invention, the color difference of the g channel in RGB color space is used for opacity parameter extraction. Because immature metaplasia and columnar epithelium tissue turns transiently white after acetic acid application but do not exhibit dysplastic tissue changes, they should not be excluded from the acetowhite region of interest. These tissue regions usually exhibit a minor opacity change. Therefore the present invention applies a two-step mean shift clustering algorithm in the color difference feature space. The first step is to segment the dominant opacity change and to remove minor opacity change. The second step is to segment the most opaque change from the foreground region obtained in the first step. An opacity parameter is computed as the mean color difference of the most opaque region. The most opaque region is defined as the region with the largest mean color difference. The opacity parameter is expressed by the following formula:

$$\text{Opacity} = \frac{1}{(2^n - 1)\Omega} \left[ \sum_{i,j} (f_k^*(i,j) - g_k(i,j))^p * r(i,j) \right]^{\frac{1}{p}} \quad (8)$$

where n is the number of bits of the image, $f^*_k$ is the registered pre-acetic acid image, and $g_k$ is the selected post acetic acid image, both at k band (k=1, 2, 3). The symbol r is the most opaque region extracted from the clustering algorithm in binary form. The symbol $\Omega$ is the number of foreground pixels in the opaque region r. The p norm metric is used in the equation. In the presently preferred implementation, p is set to 1, and the a band CIE-Lab color space is used.

The opacity parameter captures the percentage of change in pixel values (or DN or Digital Number) in a certain color space, in a certain region of interest, of a pair of registered cervical images.

Mosaic and punctation detection preferably includes detection of mosaic blood vessels, classification of mosaic blood vessels into coarse and fine based on the mean intercapillary distance, detection of punctation blood vessels, and classification of punctation vessels into coarse and fine based on the mean intercapillary distance (W. Li and A. Poirson, Detection and characterization of abnormal vascular patterns in automated cervical image analysis, *Lecture Notes in Computer Science—Advances in Visual Computing* 4292, Second International Symposium, ISVC 2006, Lake Tahoe, Nev., November 2006 Proceedings, Part II, 627-636 (Springer 2006), incorporated herein by reference)

Atypical vessel extraction preferably detects atypical vessels by applying a pre-processing stage for contrast enhancement, a segmentation stage to identify regions of interest, and a post-processing stage to determine the final region of interest. The pre-processing stage preferably smooths the image and suppresses high intensity components using a top hat filter; enhances the contrast of the image using a top hat and bottom hat filter; enhances the red component of the image; and then enhances the contrast of the red component of the image. The segmentation stage preferably identifies regions of interest for atypical vessels by locating regions of maximum texture and maximum gradient information in the image and calculating the intersection of that information. The post-processing stage preferably identifies and removes features that are unrelated to atypical vessels and further refines the image using known color, shape and size information on atypical vessels to create an output image with a final region of interest (as described in co-pending, commonly assigned patent application entitled "Methods for Detection and Characterization of Atypical Vessels in Cervical Imagery" filed Aug. 1, 2008, Ser. No. 12/221,328, incorporated herein by reference).

The outputs of the anatomic feature extraction, acetowhite feature extraction, mosaic and punctation are certain variables (as described in FIG. 2) which serve as inputs for a tissue classification method (described below).

(2) The Tissue Classification Method

Design

Preferably the design of this tissue classification method uses a rule-based classifier. The idea is not to rely on a single classifier rule (except possibly for the opacity parameter, as described below), but to use a set of classifier rules and to combine the predictions of multiple classifier rules. The purpose of a multiple-classifier scheme is to reduce variance and bias. All the classifier rules are applied to cervical tissue and the final prediction is obtained by applying selected classifier rules serially. The current invention can be combined with any statistical learning approach to form a classifier ensemble, such as Support Vector machine and Conditional Random Field (CRF) (Lafferty, J., McCallum, A., Pereira, F.: Conditional random fields: Probabilistic models for segmenting and labeling sequence data. In: *Proc. 18th International Conf. on Machine Learning*, Morgan Kaufmann, San Francisco, Calif. (2001) 282-289, incorporated herein by reference).

Simulated Colposcopic Index (SCI)

Figure 2:
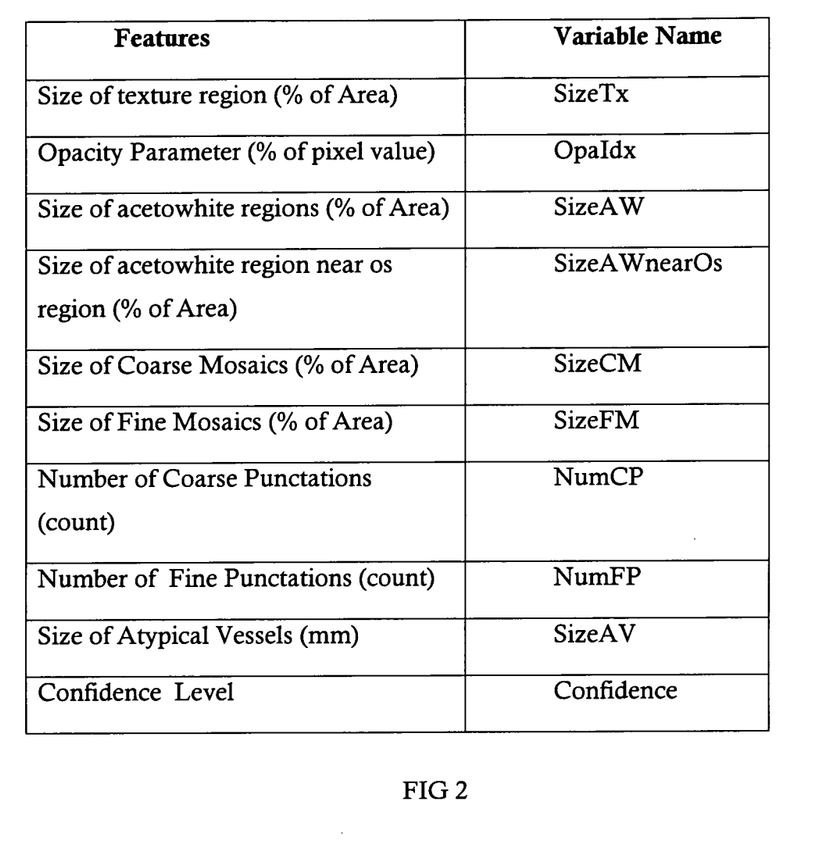
FIG. 2 is a list of the input parameters for the tissue classification method.
Figure 3:
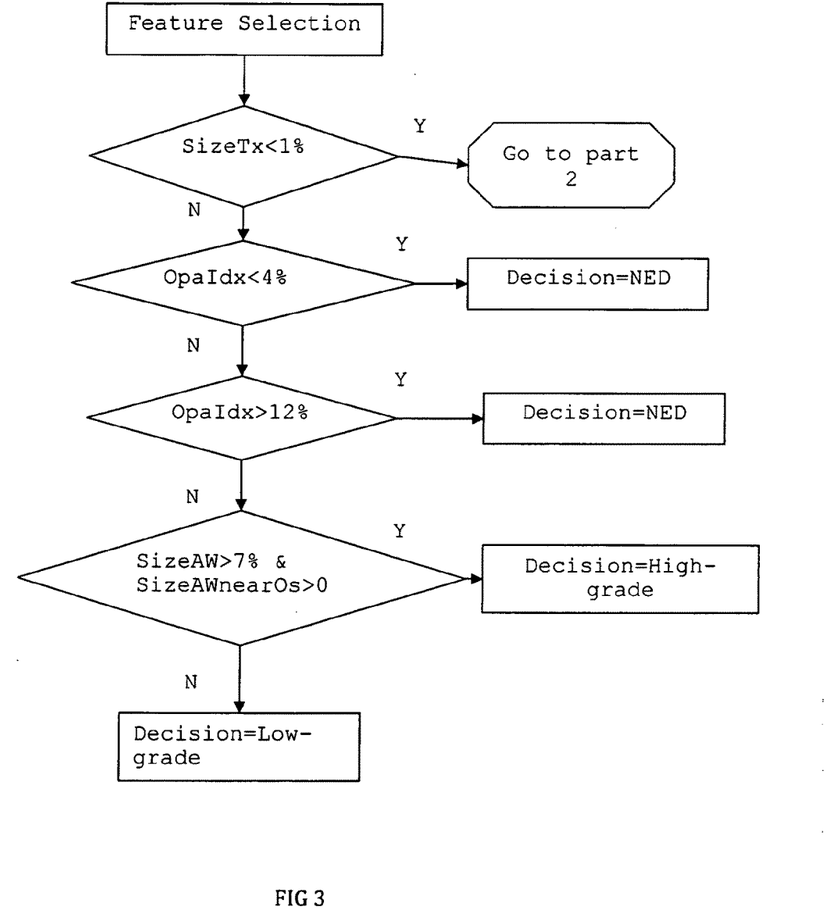
FIG. 3 is Part I of a tissue diagnosis scheme.
Figure 4:
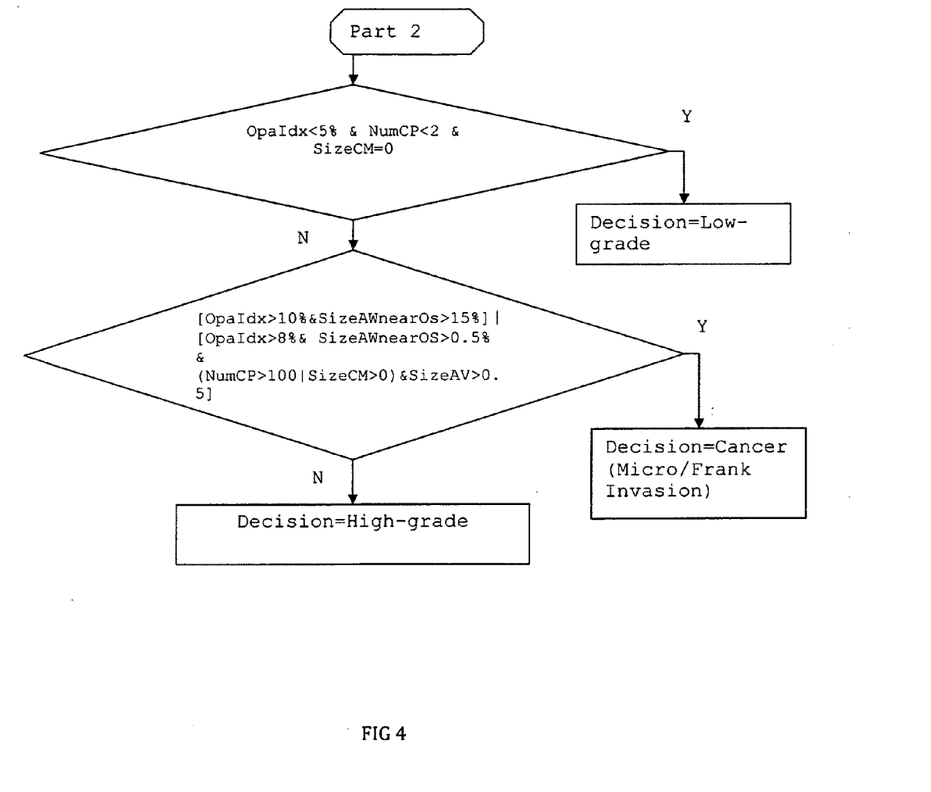
FIG. 4 is Part II of a tissue diagnosis scheme.

This tissue classification method provide a simulated colposcopic index (SCI) that is designed to provide a base diagnosis for each subject, based on the variables described in FIG. 2. The output is the determination of the type of lesions in an image. A two part diagnosis scheme is outlined in FIGS. 3 and 4. In part I (FIG. 3), first the size of a texture region (expressed as a percentage of the area of the cervix) is evaluated. If the texture region is approximately less than 1% of the area of the cervix, the user is directed to part II of the analysis (FIG. 4). If not, then the opacity parameter is evaluated. If the opacity parameter is less than approximately 4% of the pixel values (brightness in a digital image—for an 8 bit image, in which brightness is defined by 8 digits of 0s and 1s, pixel value ranges from 0 (total darkness) to 255 (highest possible brightness), for a 16 bit image, in which brightness is defined by 16 digits of 0s and 1s, pixel value ranges from 0-65535—pixel value is sometimes referred to as "Digital Number" or "DN".) or greater than approximately 12% of pixel value, then a diagnostic decision of "NED" (No evidence of disease) is given. If not, then the size of the acetowhite regions and acetowhite regions near the os region are evaluated. If the size of the acetowhite region is greater than 7% of the area of the cervix, and if the size of the acetowhite region near the os is greater than 0% of the area of the cervix then a decision of "high grade" (high grade lesion) is given. If not, then a decision of "low-grade" (low grade lesion) is given.

In part II, the first step evaluates whether the opacity parameter is less than 5% of pixel value, the number of coarse punctations are less than 2, and the size of coarse mosaics is equal to 0% of the total area of the cervix. If the answer is yes, then a decision of "low grade" is given. If the answer is no, then the method goes on to the second step.

In the second step, if the opacity parameter is larger than 10% and there is more than 15% acetowhite region near os region, the decision is "Cancer". Or if the opacity parameter is larger than 8%, there is more than 0.5% acetowhite region near os region, the number of coarse punctation vessels is larger than 100, there are some coarse mosaic vessels, and the size of atypical blood vessels is larger than 0.5 mm, the decision is also "Cancer".

If the answer is yes, then the decision is "Cancer". If the answer is no, then the decision is "high-grade".

Figure 5:
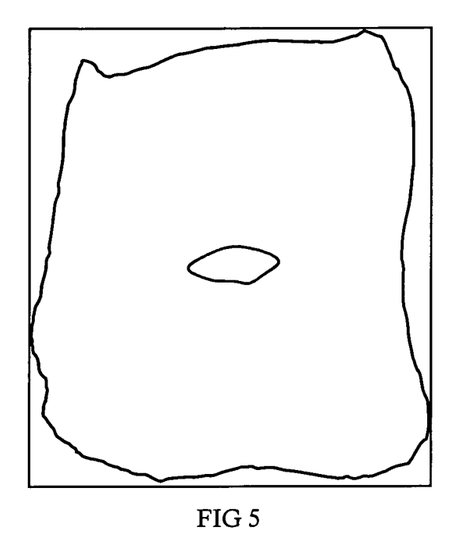
FIG. 5 is a black and white line drawing based on a photograph of an example of a NED (No Evidence of Disease) subject.
Figure 6A:
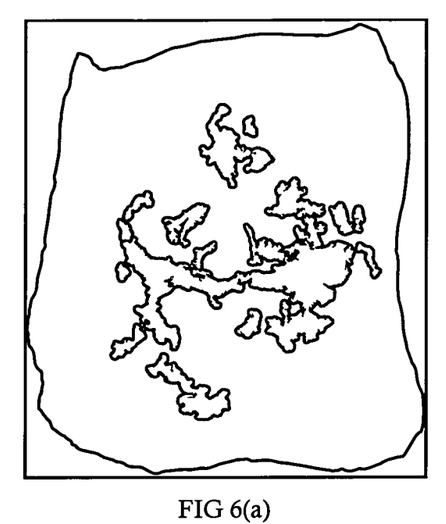
FIG. 6(a) is a black and white line drawing based on a photograph of an example of low-grade disease subject.
Figure 7A:
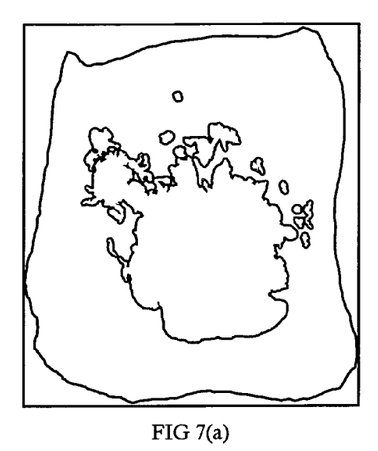
FIG. 7(a) is a black and white line drawing based on a photograph of an example of cancer subject.
Figure 8A:
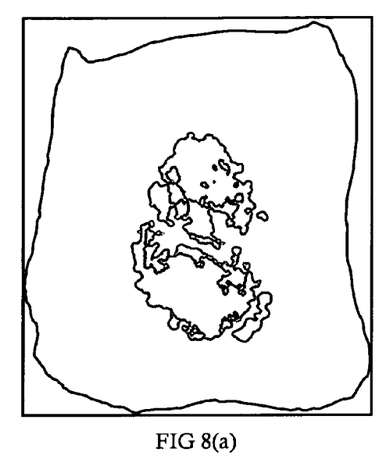
FIG. 8(a) is a black and white line drawing based on a photograph of an example of a high-grade disease subject.

FIG. 5 depicts an example of NED subject in which the size of the texture region is less than 1% of the total area of the cervix and the opacity parameter is less than 4% of pixel value. FIG. 6(*a*) shows an example of a low-grade subject in which the size of the texture region is greater than 1% of the total area of the cervix. FIG. 7(a) is an example of a cancer subject in which the size of the texture region is greater than 1% of the total area of the cervix; the opacity parameter is greater than 10% of pixel value, and size of the acetowhite region near the os region is greater than 15% of the total area of the cervix. FIG. 8(a) is an example of a high-grade subject in which the size of the texture region is greater than 1% of the total area of the cervix.

It should be noted that in the present invention, the opacity parameter is combined with other classifier rules, including mosaic, punctation, and atypical blood vessels, to make a diagnostic decision using a set of classifier rules. Thus, the opacity parameter classifier rule's thresholds are changed in this invention (to make a more detailed and accurate diagnosis) from the 5% threshold in the patent application described above that disclosed the opacity parameter. However, the opacity parameter provides high predictability and therefore can be used alone, with the 5% threshold, in lower cost or simpler devices or processes.

Disease Location

Figure 6B:
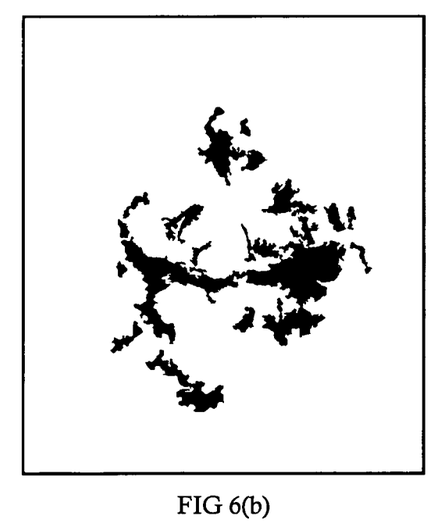
FIG. 6(b) is a detection mask (with dark areas indicating location of detection and light areas indicating background) based on an image processed photograph of the corresponding low-grade disease location of the subject in FIG. 6(a).
Figure 7B:
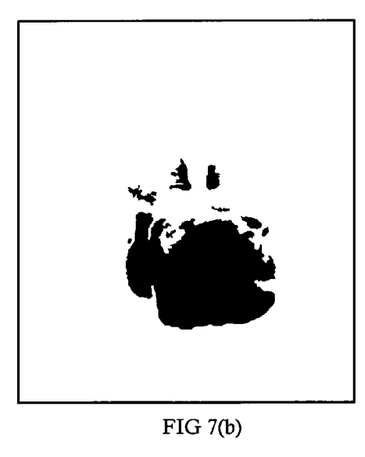
FIG. 7(b) is a detection mask (with dark areas indicating location of detection and light areas indicating background) based on an image processed photograph of the corresponding high-grade disease location of the subject in FIG. 7(a).
Figure 7C:
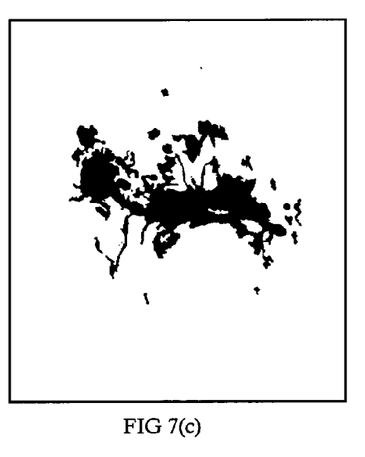
FIG. 7(c) is a detection mask (with dark areas indicating location of detection and light areas indicating background) based on an image processed photograph of the corresponding low-grade disease location of the subject in FIG. 7(a).
Figure 8B:
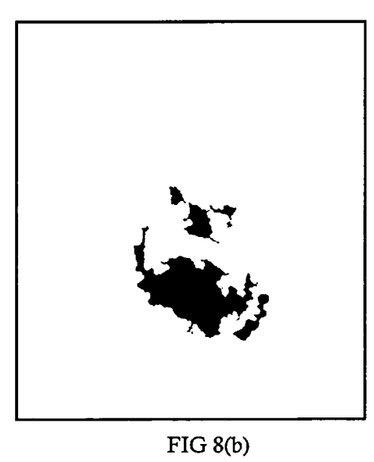
FIG. 8(b) is a detection mask (with dark areas indicating location of detection and light areas indicating background) based on an image processed photograph of the corresponding high-grade disease location of the subject in FIG. 8(a).
Figure 8C:
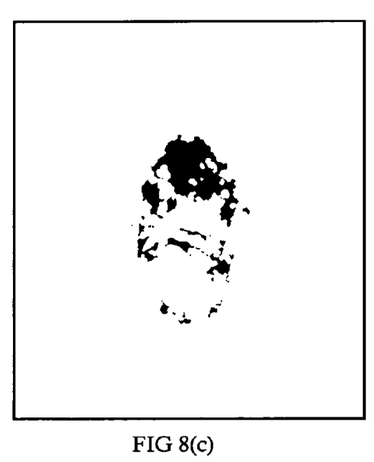
FIG. 8(c) is a detection mask (with dark areas indicating location of detection and light areas indicating background) based on an image processed photograph of the corresponding low-grade disease location of the subject in FIG. 8(a).

Under the patient diagnosis, disease location is defined as the combination of the colposcopic signs for different grades of lesions. A mask is a black and white image. The black (dark) area is the foreground that indicates where the lesion is, and the white (bright) area is the background. The high-grade lesion mask is defined as the union of mask images of acetowhite, coarse mosaic, coarse punctations, and atypical vessels. The level of acetowhite mask depends on the opacity parameter and patient diagnosis. Similarly, the low-grade lesion mask is defined as the union of mask image of acetowhite fine mosaic, and fine punctations. The level of acetowhite mask depends on the opacity parameter and patient diagnosis. Examples of high-grade masks can be seen in FIGS. 7(b) and 8(b), displayed as dark areas. Examples of low grade masks can be found in the above FIG. 6(b), FIG. 7(c) and FIG. 8(c), displayed as dark areas.

Confidence Level

Confidence level can be determined through three aspects: image quality, adequacy of feature extractions, and patient's demographic data. The present invention assumes the acquisition of high quality image data by the IQA procedure (as described in co-pending, commonly assigned patent application entitled "Method to Provide Automated Quality Feedback to Imaging Devices to Achieve Standardized Images" filed Mar. 14, 2008, Ser. No. 12/075,890, incorporated herein by reference), but any other method of acquiring high quality images can be used. Thus, only adequacy of feature extraction and patient's demographic data are considered. Adequacy is preferably computed by evaluating the feature extraction status into an array including the following categories: the ratio of the cervix region to (over) the size of image plane; the ratio of squamous region to the cervix region; the size and location of os region; and possible presence of mucus and other obstruction like IUD (intra uterine device). If the output (a number) is within a pre-defined range it is a "pass". If the output is not within a pre-defined range it is a "fail". For example, if the ratio of the cervix region over the size of the image plane is in the range of 30% to 80%, it is a "pass", otherwise, it is a "fail" for this category. The confidence level is derived by the percentage of "pass" among all of the categories. The final confidence level is decreased by a percentage factor (10-20%) if the patient is too young (less than 25 years old) or too old (more than 60 years old), or had surgery before the exam. Severe cases such as cancer rarely happen in patients less than 25 years old. Due to the biological basis of the features observed, older patients tend to show less pronounced changes.

While the present invention has been particularly shown and described with reference to the embodiments described in the detailed description and illustrated in the figures, it will be understood by those skilled in the art that various changes in detail may be effected therein without departing from the spirit and scope of the invention. Accordingly, no limitations are to be implied or inferred except as specifically and explicitly set forth in the claims.

Industrial Applicability

The present invention can be used to provide an unsupervised rule-based tissue classification method that utilizes reliable colposcopic scoring features to provide a diagnosis of "no evidence of disease", low-grade dysplasia, high-grade dysplasia, or cancer, and also to provide locations of high-grade lesions, and the confidence level of the diagnosis. This diagnosis can be used directly or suggested to a physician or other health care provider.

What is claimed is:

1. A rule-based unsupervised process for classifying cervical tissue into a diagnostic class, comprising:
    collecting at least two digital color images of a patient cervix, one image of the patient cervix before the application of acetic acid to cervical tissue, and one image of the patient cervix after the application of acetic acid to cervical tissue;
    determining, based on the collected digital color images, variables for a cervical tissue classification procedure, the variables including:
        the size of the texture region, an opacity parameter, the size of acetowhite regions, the size of acetowhite region near os region, the size of coarse mosaics, the size of fine mosaics, the number of coarse punctations, the number of fine punctations, and the size of atypical vessels,
        wherein the opacity parameter is expressed by the following formula:

$$\text{Opacity} = \frac{1}{(2^n - 1)\Omega} \left[ \sum_{i,j} (f_k^*(i, j) - g_k(i, j))^p * r(i, j) \right]^{\frac{1}{p}},$$

where n is the number of bits of the image, $f^*_k$ is the registered pre-acetic acid image and $g_k$ is the post-acetic acid image both at k band (k=1, 2, 3), r is the most opaque region extracted from the clustering algorithm in binary form, $\Omega$ is the number of foreground pixels in the opaque region r, and p is the norm metric;
    serially applying, using a computer, a set of classifier rules to said cervical tissue, based on the determined variables, according to a diagnosis scheme, the classifier rules including:
        determining the size of a texture region relative to the area of the cervix, determining an opacity parameter relative to one or more thresholds, and optionally including one or more classifier rules selected from the group consisting of:
        determining the size of acetowhite regions relative to area of the cervix, determining the size of acetowhite regions near os region relative to area of the cervix, determining the number of coarse and fine punctations, determining the size of coarse and fine mosaics relative to area of the cervix, and determining the size of atypical blood vessels relative to a threshold; and obtaining, based on the serial application of classifier rules according to the diagnosis scheme, a patient diagnosis classification of no evidence of disease (NED), low-grade dysplasia, high-grade dysplasia, or cancer.

2. A process according to claim 1, wherein the rules of the diagnosis scheme include:

when said texture region is greater than approximately 1% of the area of the cervix, and the opacity parameter is less than approximately 4% of the pixel value or greater than approximately 12% of the pixel value, a diagnosis of no evidence of disease is obtained.

3. A process according to claim 1, wherein the rules of the diagnosis scheme include:

when said texture region is greater than approximately 1% of the area of the cervix, said opacity parameter is between approximately 4% of the pixel value and approximately 12% of the pixel value, the size of the acetowhite region is greater than 7% of the area of the cervix, and the size of the acetowhite region near the os is greater than 0% of the area of the cervix, a diagnosis of high grade dysplasia is obtained.

4. A process according to claim 1, wherein the rules of the diagnosis scheme include:

when said texture region is greater than approximately 1% of the area of the cervix, said opacity parameter is between approximately 4% of the pixel value and, approximately 12% of the pixel value, the size of the acetowhite region is less than 7% of the area of the cervix, and there is no acetowhite region near the os, a diagnosis of low grade dysplasia is obtained.

5. A process according to claim 1, wherein the rules of the diagnosis scheme include:

when said texture region is less than approximately 1% of the area of the cervix, the opacity parameter is less than 5% of the pixel value, the number of coarse punctations is less than 2, and there are no coarse mosaic vessels, a diagnosis of low grade dysplasia is obtained.

6. A process according to claim 1, wherein the rules of the diagnosis scheme include:

when said texture region is less than approximately 1% of the area of the cervix, the opacity parameter is greater than 10% of the pixel value, and the size of the acetowhite region near the os is greater than 15% of the area of the cervix, a diagnosis of cancer is obtained.

7. A process according to claim 1, wherein the rules of the diagnosis scheme include:

when said texture region is less than approximately 1% of the area of the cervix, the opacity parameter is greater than 8% of the pixel value, the size of the acetowhite region near the os is greater than 0.5% of the area of the cervix, the number of coarse punctations is greater than 100, there are no coarse mosaic vessels, and the size of atypical vessels is greater than 0.5 millimeters, a diagnosis of cancer is obtained.

8. A process according to claim 1, wherein the rules of the diagnosis scheme include:

when said texture region is less than approximately 1% of the area of the cervix, the opacity parameter is greater than 5% of the pixel value, the size of the acetowhite region near the os is less than 0.5% of the area of the cervix, the number of coarse punctation vessels is less than 100, coarse mosaic vessels are not present, and the size of atypical blood vessels is less than 0.5 mm, a diagnosis of high grade dysplasia is obtained.

9. A process according to any one of claims 1 to 8, further comprising:

determining a confidence level of the diagnosis based on at least on the age of the patient; and reducing the confidence level by between approximately 10% and approximately 20% if the patient is below 25 years old or over 60 years old.

10. A rule-based unsupervised process for classifying cervical tissue into a class, comprising:

collecting at least two digital color images of a patient cervix, one image of the patient cervix before the application of acetic acid to cervical tissue, and one image of the patient cervix after the application of acetic acid to cervical tissue;

determining, based on the collected digital color images, variables for a cervical tissue classification procedure, the variables including:

the size of the texture region, an opacity parameter, the size of acetowhite regions, the size of acetowhite region near os region, the size of coarse mosaics, the size of fine mosaics, the number of coarse punctations, the number of fine punctations, and the size of atypical vessels;

serially applying, using a computer, a set of classifier rules to said cervical tissue, based on the determined variables, according to a diagnosis scheme; and obtaining a patient diagnosis classification of no evidence of disease (NED), low-grade dysplasia, high-grade dysplasia, or cancer, based on the application of classifier rules according to the diagnosis scheme, wherein the schema consists of the following classifier rules:

when said texture region is greater than approximately 1% of the area of the cervix, and the opacity parameter is less than approximately 4% of the pixel value or greater than approximately 12% of the pixel value, a diagnosis of no evidence of disease is obtained;

when said texture region is greater than approximately 1% of the area of the cervix, said opacity parameter is between approximately 4% of the pixel value and approximately 12% of the pixel value, the size of the acetowhite region is greater than 7% of the area of the cervix, and if the size of the acetowhite region near the os is greater than 0% of the area of the cervix, a diagnosis of high grade dysplasia is obtained;

when said texture region is less than approximately 1% of the area of the cervix, the opacity parameter is greater than 5% of the pixel value, the size of the acetowhite region near the os is less than 0.5% of the area of the cervix, the number of coarse punctation vessels is less than 100, coarse mosaic vessels are not present, and the size of atypical blood vessels is less than 0.5 mm, then a diagnosis of high grade dysplasia is obtained;

when said texture region is greater than approximately 1% of the area of the cervix, said opacity parameter is between approximately 4% of the pixel value and approximately 12% of the pixel value, the size of the acetowhite region is less than 7% of the area of the cervix, and there is no acetowhite region near the os, a diagnosis of low grade dysplasia is obtained;

when if when said texture region is less than approximately 1% of the area of the cervix, the opacity parameter is less than 5% of the pixel value, the number of coarse punctations is less than 2, and there are no coarse mosaic vessels, a diagnosis of low grade dysplasia is obtained;

when said texture region is less than approximately 1% of the area of the cervix, the opacity parameter is greater than 10% of the pixel value, the size of the acetowhite region near the os is greater than 15% of the area of the cervix, a diagnosis of cancer is obtained; and when said texture region is less than approximately 1% of the area of the cervix, the opacity parameter is greater than 8% of the pixel value, the size of the acetowhite region near the os is greater than 0.5% of the area of the cervix, the number of coarse punctations is greater than 100, there are no coarse mosaic vessels, and the size of abnormal vessels is greater than 0.5 millimeters, a diagnosis of cancer is obtained.

11. A process according to claim 10, further comprising:
determining a confidence level of the diagnosis based on at least on the age of the patient; and
reducing the confidence level by between approximately 10% and approximately 20% if the patient is below 25 years old or over 60 years old.

* * * * *